United States Patent [19]

Sharma et al.

[11] Patent Number: 4,702,819
[45] Date of Patent: Oct. 27, 1987

[54] PROCESS FOR SEPARATION OF HYDROCARBON MIXTURES

[75] Inventors: Shanmuk Sharma, Houston; Donnie K. Hill, Woodlands; Charles A. Durr, Houston, all of Tex.

[73] Assignee: The M. W. Kellogg Company, Houston, Tex.

[21] Appl. No.: 944,319

[22] Filed: Dec. 22, 1986

[51] Int. Cl.⁴ .............................................. C10G 7/00
[52] U.S. Cl. .................... 208/354; 208/351; 208/355; 203/DIG. 19; 203/71
[58] Field of Search ............... 208/351, 352, 354, 355, 208/353, 358; 203/74, 81, 73, 71, DIG. 19

[56] References Cited

U.S. PATENT DOCUMENTS

| | | | |
|---|---|---|---|
| 3,173,859 | 3/1965 | Chambers | 208/354 |
| 3,536,610 | 10/1970 | Stork | 208/358 |
| 4,308,131 | 12/1981 | Bannon | 208/353 |
| 4,415,443 | 11/1983 | Murphy | 208/355 X |

Primary Examiner—Andrew H. Metz
Assistant Examiner—Glenn Caldarola

[57] ABSTRACT

A process for separating gaseous or liquid hydrocarbons in first and second fractionation zones wherein the first fractionation zone employs a side reboiler discharging below the side draw point. A vapor sidestream is removed from the first fractionator below the side draw point and introduced to the second fractionator. The flow scheme permits control of the first fractionator bottoms temperature to match available low level waste heat which may therefore be used in fractionator reboiling duty.

4 Claims, 2 Drawing Figures

PROCESS FOR SEPARATION OF HYDROCARBON MIXTURES

This invention relates to a process for separation of hydrocarbon mixtures in two fractionation zones. More particularly, the invention relates to a method for prefractionation of flow withdrawn from the first fractionation zone and introduced to the second fractionation zone. The process of the invention is applicable to both normally liquid and normally gaseous hydrocarbons and is particularly well suited to production of $C_3$–$C_4$ liquefied petroleum gas (LPG) in, for example, refinery gas separations and natural gas liquids separations. In separation of normally gaseous hydrocarbons, the starting gas stream to the process of the invention may contain substantial amounts of carbon dioxide or nitrogen resulting from well injection of these gases for enhanced oil recovery operations.

According to the invention, a hydrocarbon mixture optionally containing non-hydrocarbon gases is introduced to at least one upper feed point of a first fractionation zone from which a first overhead vapor stream is recovered as well as a first bottoms liquid stream. The first bottoms liquid stream is introduced to an intermediate feed point of the second fractionation zone from which a second overhead vapor stream and a second bottoms liquid stream are withdrawn. A liquid sidestream is removed from an intermediate side draw point of the first fractionation zone, reboiled, and re-introduced to the first fractionation zone at a location below the intermediate side draw point while a vapor sidestream is taken from below the intermediate liquid side draw point, preferably below the side reboiler return point, and introduced to an upper feed point of the second fractionation zone. Withdrawal of the vapor sidestream permits control of the primary fractionator bottoms temperature to match waste heat from a warmer refrigerant stream available, for example, from an external refrigerant system employed for upstream gas dehydration and cooling. Use of the warmer refrigerant streams for primary fractionator reboiling duty not only deletes stream reboiling requirements but also reduces cooling water requirements of the external refrigerant system. In most instances, reboiling requirement of the secondary fractionator is also reduced.

BRIEF DESCRIPTION OF THE DRAWINGS

Referring to FIG. 1, hydrocarbon mixtures are introduced to a first fractionation zone indicated as distillation column 36 which is equipped with overhead vapor line 37, bottom reboiler system 44, and side reboiler system 45. The side reboiler vaporizes liquid withdrawn from intermediate tray 46 and discharges the resulting vapor into the column at a point below the intermediate liquid side draw point. When the hydrocarbon mixtures are derived from refinery gas for production of liquefied petroleum gas, that is a $C_3/C_4$, the first fractionation zone will be at a pressure typically between 4 and 28 $kg/cm^2a$ and the mixture entering the first fractionation zone will be principally $C_2$ and heavier gases with minor amounts of methane. Preferably, the entering mixture will be prefractionated into discrete portions shown in the drawing as streams 35, 19/22, and 23 which are respectively at temperatures of $-65°$ C., $-35°$ C., and $-4°$ C. and introduced to the column at a respective plurality of upper feed points. If upstream prefractionation and refrigeration recovery results in closer temperature grouping of these streams, they may be combined and introduced to the column at a single upper feed point.

Figure 1:
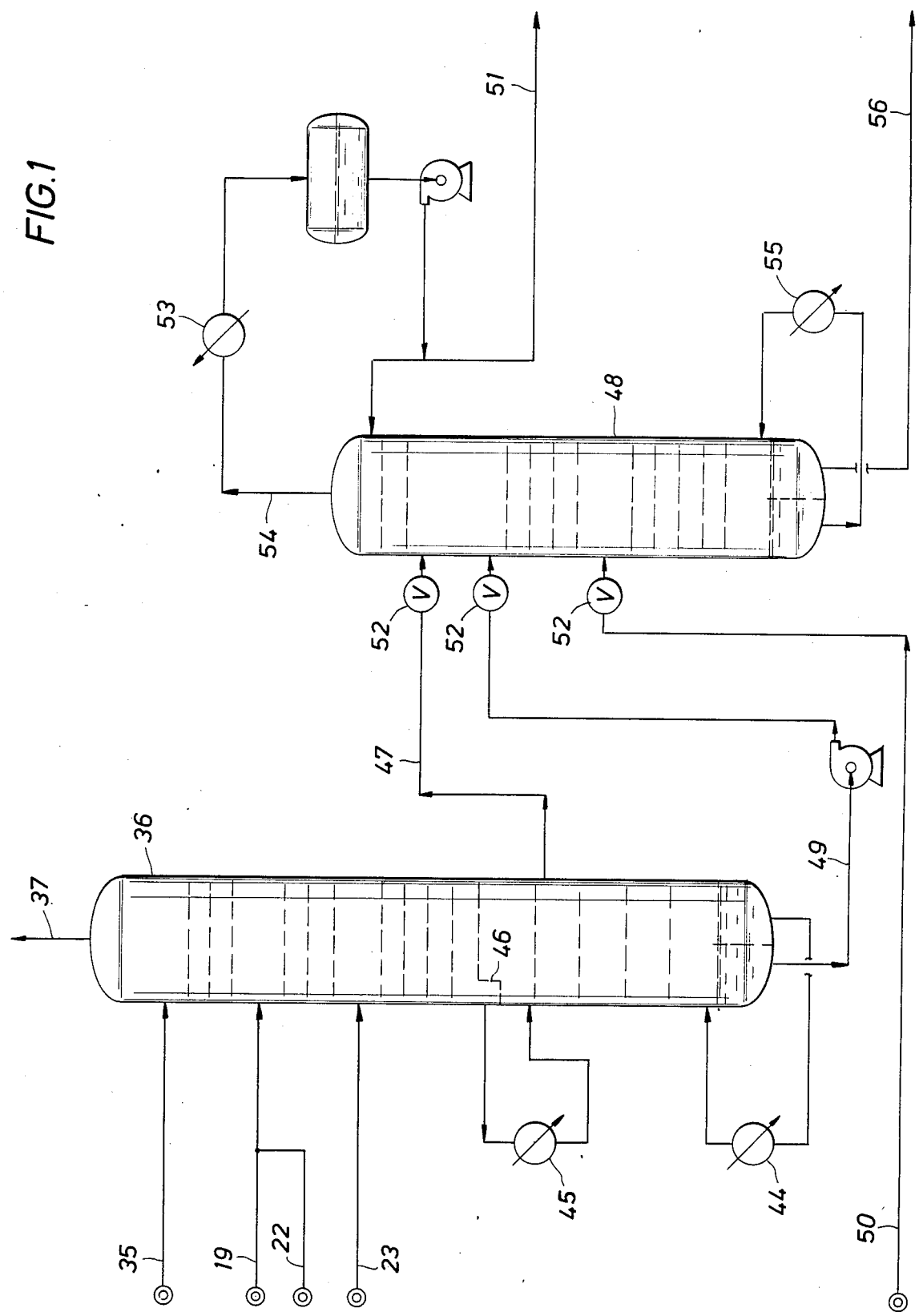
FIG. 1 is a flow diagram of the process of the invention.

A first overhead vapor stream rich in ethane is removed from column 36. Preferably, refrigeration will be recovered from this cold intermediate pressure stream prior to its delivery as product gas.

A hydrocarbon vapor sidestream comprised principally of $C_3$ and $C_4$ gases is removed from below the intermediate liquid side draw point of column 36 and introduced via line 47 to a second fractionation zone indicated as column 48. Similarly, a first bottoms liquid stream comprised principally of $C_3+$ liquids is recovered from column 36 and introduced via line 49 to an intermediate point of the second fractionation zone below the vapor feed point of line 47. Typically, a liquid stream rich in $C_5+$ hydrocarbons removed from the starting refinery gas will also be introduced to the second fractionation zone via line 50 in order to separate the $C_4$ component therefrom for recovery with the LPG product in line 51.

For optimum LPG production, the second fractionation zone will have an overhead vapor temperature between 20° and 50° C. which may be attained by operating column 48 at a pressure between 3 and 14 $Kg/cm^2$ and expanding feed streams 47, 49, and 50 through valves 52. The refrigeration thereby obtained supplements refrigeration provided by reflux and product chiller 53 which cools the second overhead vapor stream 54 recovered from the second fractionation zone. Heat required for operation of column 48 is provided by bottom reboiler system 55 and a light gasoline product is recovered through the second bottoms liquid stream 56.

Reboiling bottom liquids in column 36 and column 48 represents a process inefficiency when steam is employed. By the process of the invention, however, the bottom reboiler duty in column 48 is reduced by withdrawing a portion of the column 48 feed as a vapor sidestream from column 36 instead of withdrawing all of the feed as liquid from column 36 bottoms in accordance with known practice. As previously noted, the resulting controllable bottoms temperature in column 36 permits use of warm refrigerant as the heat source in reboilers 44 and 45 in place of more costly steam.

Figure 2:
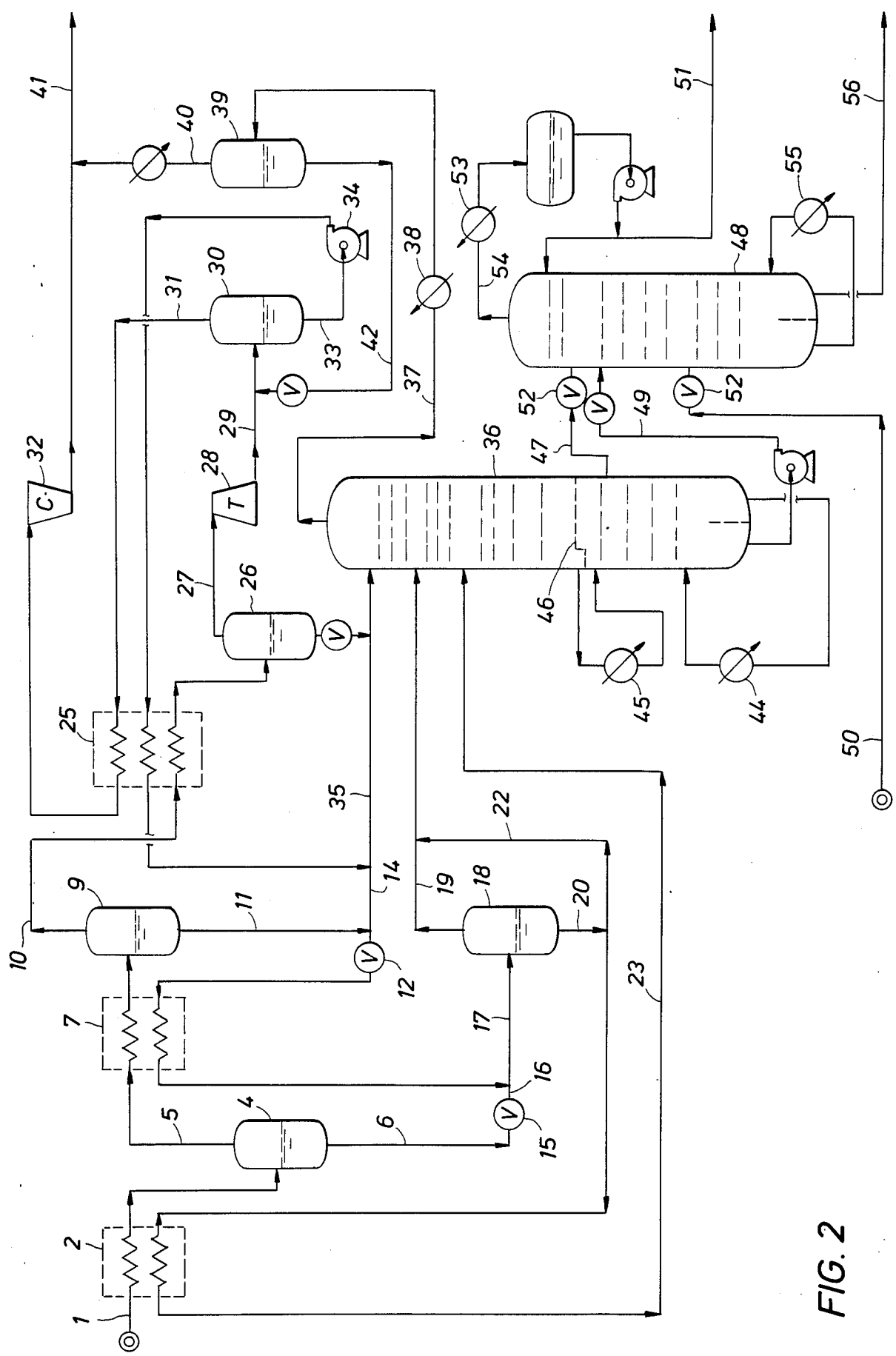
FIG. 2 is an overall flow diagram of a process for separation of refinery gases with the principal object of LPG production and illustrates use of the invention in the de-ethanizer column section of a refinery gas separations flow scheme.

Referring now to FIG. 2 in which reference numerals are common with those in FIG. 1, a dried refinery gas stream substantially free of acid gas and $C_5+$ hydrocarbon components is introduced to the LPG separation system through line 1 at a pressure of 12 $kg/cm^2a$. A typical stream composition is:
Hydrogen: 9.2 mole percent,
Nitrogen: 4.7 mole percent,
$CH_4$: 45.6 mole percent,
$C_2H_4/C_2H_6$: 28.4 mole percent,
$C_3H_6/C_3H_8$: 9.2 mole percent,
$C_4H_8/C_4H_{10}$: 2.6 mole percent,
$C_5+$: 0.3 mole pecent.

This high pressure gas stream is cooled to $-29°$ C. in exchanger 2 and flashed in drum separator 4. The vapor stream from separator 4 is further cooled to $-55°$ C. in exchanger 7 and flashed in separator 9 from which the vapor portion is further cooled in exchanger 25 to −68° C. and flashed in separator 26 to yield a high pressure gas stream containing substantially all of the starting hydrogen and nitrogen, most of the methane, and about half of the $C_2$ components. This methane-rich stream is expanded across turbine 28, which extracts shaft work for compressor 32, and discharged at a temperature of −92° C. and pressure of 4 kg/cm$^2$a to separator 30 where more of $C_2+$ components are separated as liquid. Refrigeration is recovered from the remaining methane-rich vapor in line 31 through a series of heat exchangers of which only exchanger 25 is shown and the resulting product gas is recompressed in compressor 32 to delivery pressure of 5 kg/cm$^2$a in line 41.

The cold liquid stream 11 from separator 9 is expanded across valve 12 to a pressure of 7 kg/cm$^2$a and provides refrigeration to vapor stream 5 entering exchanger 7. If desired, a portion of this stream may be expanded and taken forward in the process through line 14. Following refrigeration recovery, stream 13 is combined with cold stream 16 which results from expansion of separator 4 liquid and the resulting mixed intermediate pressure stream in line 17 is flashed in separator 18. The resulting liquid stream 20 which contains most of the $C_3+$ components of the starting gas in line 1 provides an enhanced source of refrigeration for the starting gas in exchanger 2 from which it is recovered as stream 23 at a temperature of −4° C. and introduced to de-ethanizer column 36.

The balance of stream 20 not needed in exchanger 2 is sent forward through line 22 and combined with vapor leaving separator 18 prior to introduction to column 36. Since stream 23 is warmer than combined streams 19 and 22, it is evident that stream 17 has been prefractionated into discrete portions prior to introduction to column 36 and thereby reduces separation requirements of the column.

Liquid from separator 26 is expanded across a valve, combined wtih flow in line 35 and introduced to an upper feed point of column 36. Since this stream is substantially colder than the two lower feeds, it represents an additional prefractionation of the starting gas. De-ethanizer column 36 overhead gas is principally $C_2$ components of the starting gas and is cooled to −54° C. and flashed in separator 39. Refrigeration is recovered from the resulting vapor stream 40 which is principally $C_2$ hydrocarbons and methane and the resulting warmer stream then combined with product gas discharged from compressor 32.

Since separator 39 is over 1 kg/cm$^2$ higher in pressure than separator 30, additional refrigeration is recovered by expanding liquid stream 42 into separator 30 which operates at the discharge pressure of turbine 28. The resulting very cold liquid 33 from separator 30 is increased to column pressure by pump 34 and refrigeration is recovered from the stream in exchanger 25. The resulting relatively warmer stream 35 is then combined with underflow from separator 26 and introduced to the de-ethanizer column.

The function of de-ethanizer column 36 is of course to remove $C_2$ and lighter feed streams from what is to be the desired LPG product removed from the column bottoms. Since the bottoms stream 49 also contains a minor amount of $C_5+$ material, it is further fractionated in debutanizer column 48 which has the principal function of separating $C_3/C_4$ components from a previously separated light gasoline stream introduced through line 50. In customary operation, column 36 bottoms are reboiled through exchanger 44 and column 48 bottoms are reboiled through exchanger 55 while column 48 overhead is cooled and refluxed through exchanger 53. The final separations carried out in column 48 result in recovery of an LPG product stream through line 51 and a light gasoline stream through line 56.

With this two column operation, it is apparent that bottom liquids from column 36 removed through line 49 must again be vaporized in column 48 by reboiler 55. In order to reduce this vaporization requirement, a light liquid side stream is removed from an intermediate tray 46 in column 36, vaporized in side reboiler 45 and discharged back into the column below the intermediate tray and a vapor side stream is withdrawn from another intermediate point of column 36 and introduced to column 48 through line 47. Needless to say, reboiler 46 displaces duty that would otherwise be required in reboiler 44.

We claim:

1. A process for separating hydrocarbons in a first fractionation zone having a bottoms reboiler and a second fractionation zone having a bottoms reboiler which comprises:
    (a) introducing a hydrocarbon mixture to at least a first upper feed point of the first fractionation zone and recovering therefrom a first overhead vapor stream and a first bottoms liquid stream;
    (b) introducing the first bottoms liquid stream to an intermediate feedpoint of the second fractionation zone;
    (c) reboiling a hydrocarbon liquid sidestream removed from an intermediate liquid side draw point of the first fractionation zone and reinjecting the resulting reboiled hydrocarbon sidestream into the first fractionation zone at a point below the intermediate liquid side draw point;
    (d) removing a hydrocarbon vapor sidestream from below the intermediate liquid side draw point of the first fractionation zone;
    (e) introducing the hydrocarbon vapor sidestream to an upper feed point of the second fractionation zone; and
    (f) recovering a second overhead vapor stream and a second bottoms liquid stream from the second fractionation zone.

2. The process of claim 1 wherein the hydrocarbon mixture contains ethane.

3. The process of claim 2 wherein the first fractionation zone is at a pressure between 4 and 28 kg/cm$^2$a, the second fractionation zone is at a pressure between 3 and 14 kg/cm$^2$a, and the first bottoms liquid stream and the hydrocarbon vapor sidestream are expanded into the second fractionation zone.

4. The process of claim 1 wherein the hydrocarbon mixture contains $C_2$ to $C_4$ hydrocarbons, the hydrocarbon mixture is prefractionated into discrete portions and the discrete portions are introduced to a respective plurality of upper feed points of the first fractionation zone.

* * * * *